US006608677B1

(12) United States Patent
Ray et al.

(10) Patent No.: US 6,608,677 B1
(45) Date of Patent: Aug. 19, 2003

(54) MINI-LIDAR SENSOR FOR THE REMOTE STAND-OFF SENSING OF CHEMICAL/BIOLOGICAL SUBSTANCES AND METHOD FOR SENSING SAME

(75) Inventors: Mark D. Ray, Upton, NY (US); Arthur J. Sedlacek, Middle Island, NY (US)

(73) Assignee: Brookhaven Science Associates LLC, Upton, NY (US)

(*) Notice: Subject to any disclaimer, the term of this patent is extended or adjusted under 35 U.S.C. 154(b) by 317 days.

(21) Appl. No.: 09/659,202

(22) Filed: Sep. 13, 2000

Related U.S. Application Data

(63) Continuation-in-part of application No. 09/189,333, filed on Nov. 9, 1998.

(51) Int. Cl.⁷ .......................... G01J 3/44; G01N 21/65
(52) U.S. Cl. ........................................... 356/301
(58) Field of Search ............................. 356/301, 317, 356/318, 417; 250/458.1, 459.1, 461.1, 461.2

(56) References Cited

U.S. PATENT DOCUMENTS

| | | | |
|---|---|---|---|
| 3,414,354 A | 12/1968 | Siegler, Jr. | 356/75 |
| 3,625,613 A | 12/1971 | Abell et al. | 356/75 |
| 3,768,908 A | * 10/1973 | Zaromb | 356/301 |
| 4,200,801 A | * 4/1980 | Schuresko | 250/458.1 |
| 4,651,010 A | * 3/1987 | Javan | 250/458.1 |
| 4,945,249 A | 7/1990 | Grant et al. | 250/461.1 |
| RE34,153 E | 12/1992 | Benner et al. | 356/301 |
| 5,257,085 A | 10/1993 | Ulich et al. | 356/73 |
| 5,373,358 A | 12/1994 | Adachi | 364/498 |
| 5,377,004 A | 12/1994 | Owen et al. | 364/498 |
| 5,710,713 A | 1/1998 | Wright et al. | 364/498 |

OTHER PUBLICATIONS

Angel, et al. "Remote–Raman Spectroscopy at Intermediate Ranges Using Low–Power cw Lasers", Applied Spectroscopy, vol. 46, No. 7 Nov. 7, 1992, pp. 1085–1091.
Noggle, Joseph, *Physical Chemistry*, 2 ed. (1989) §14.10 pp. 886–890.
Ray, et al., "Mini Raman Laser–Radar System of *In Situ*, Stand–Off Interrogation of Surface Contamination", 19th International Laser Radar Conference Abstracts, Jul. 1998, pp 677 (NASA/CP–1998–207671/PT2).
Sedlacek, et al., "Development of Pump–and–Probe LIDAR for *In–situ* Study of Fast Atmospheric Chemical Reactions", Annual Report to the Department of Energy, Dec. 1998.

* cited by examiner

Primary Examiner—F. L. Evans
(74) Attorney, Agent, or Firm—Margaret C. Bogosian

(57) ABSTRACT

A method and apparatus for remote, stand-off, and high efficiency spectroscopic detection of biological and chemical substances. The apparatus including an optical beam transmitter which transmits a beam having an axis of transmission to a target, the beam comprising at least a laser emission. An optical detector having an optical detection path to the target is provided for gathering optical information. The optical detection path has an axis of optical detection. A beam alignment device fixes the transmitter proximal to the detector and directs the beam to the target along the optical detection path such that the axis of transmission is within the optical detection path. Optical information gathered by the optical detector is analyzed by an analyzer which is operatively connected to the detector.

31 Claims, 15 Drawing Sheets

C

B. Thuringiensis and Acetonitrile

B. Thuringiensis ($10^8$ cfu/ml)

B

A

Acetonitrile (4% by volume)

Raman Shift (cm$^{-1}$)

B. Thuringiensis and Acetontrile in Aqueous Solution
(Laser Excitation = 244 nm; Power = 50 mW)
(Stand-off Distance = 3 m)
(Integration Time = 5 minutes)
(Spectra Offset for Clarity)

Figure 15

MINI-LIDAR SENSOR FOR THE REMOTE STAND-OFF SENSING OF CHEMICAL/BIOLOGICAL SUBSTANCES AND METHOD FOR SENSING SAME

The present application is a continuation-in-part of U.S. patent application Ser. No. 09/189,333 filed on Nov. 9, 1998 and is incorporated herein by reference.

This invention was made with Government support under contract number DE-AC02-98CH10886, awarded by the U.S. Department of Energy. The Government has certain rights in the invention.

BACKGROUND OF THE INVENTION

The present invention relates to an apparatus and method for detecting chemical/biological substances which are remote or otherwise inaccessible, such as, for example, the sensing, analysis, location and identification of gases, solid or liquid materials, contaminants and pollutants. More specifically, the present invention relates to a portable mini-lidar apparatus for the remote stand-off sensing of chemical/biological agents and the method for detecting same.

A sensor having the ability for portable, remote, stand-off, high speed and efficient sensing of chemical or biological agents would be highly desirable as there are numerous civilian and military applications which require or could benefit from such a device. Such applications include the detection classification of chemical spills and seepage thereof into the land and waters, and remotely sensing the chemical or biological agents which may be intentionally released on a population.

The release of chemical or biological agents either intentionally or accidentally often requires an emergency response in order to interrogate the contamination and determine the composition and extent of the contamination. This work is typically performed by what is known in the art as "first responders" such as police or fire units which are charged with assessing the nature of the contamination in order to determine the appropriate measures of response. Heretofore, there has been no portable unit which can perform rapid in situ stand-off, non-contact detection and identification of chemical or biological agents on natural or man-made surfaces.

Typical response protocols of the prior art require that samples be collected (for example in a Biological Integrated Detection System (BIDS) sensor truck, as would be used by military personnel) and then analyzed. This requires emergency response personnel to follow the worst case protocols until the composition of the substance is identified. These procedures can be complex, time consuming, and hazardous, depending on the contaminant. Several techniques involving ion mobility (CAM sensors), surface acoustic waves, and optical detection via fiber optics are currently available for in situ, real time analysis. However, all of these methods require that some part of the instrument come in contact with the sample. This requires emergency personnel to come extremely close to the potentially hazardous substance which is being interrogated. In addition to placing a worker at risk due to his proximity to the unknown contaminant, any time an instrument comes in contact with the contaminant, it must either be disposed of in a controlled manner or thoroughly decontaminated. Both processes are expensive, time consuming and often require elaborate procedures.

Remote sensing of many common airborne chemical species by use of lidar (an acronym for light detection and ranging) devices has been in use since the late 1960's for atmospheric research and monitoring. However, these lidar systems are intended for long range detection, (i.e., hundreds of meters to kilometers) and are restricted to probing airborne chemicals. Furthermore, these units are often extremely large in size and are not suitable for use in confined spaces such as a subway system or interior spaces of residential or commercial buildings. Several techniques have been employed for determining the composition of the airborne chemical species using spectrally-dependent optical properties. One such method which has been found to be especially useful is Raman spectroscopy.

The idea of Raman stand-off detection is based on the features of Raman scattering. Raman scattering is a two-photon process that conveys information about the vibrational mode-structure of the scattering molecule. In normal Raman scattering, an incident photon of frequency ν excites a molecule from its ground electronic level to a "virtual" energy level. If the energy of this virtual level is sufficiently different from that of the nearest real level, the molecule returns quickly back to its ground level; a second photon is emitted almost instantly. If the emitted photon has the same frequency as the incident one, the process is called Rayleigh scattering. However, interaction of the incident photons with the vibrations of a molecule can shift the frequencies of the scattered photons. The shifts are equal to the frequencies of the discrete vibrational modes of the molecule. This unique set of frequency-shifts produces a spectrum that is a vibrational fingerprint of the interacting molecule.

Raman spectroscopy and infrared (IR) absorption spectroscopy are the most common types of vibrational spectroscopy and are complementary to each other. But Raman line positions and relative intensities, (i.e. Raman fingerprints) tend to be nearly independent of the physical state and/or the surrounding environment of the chemical of interest. For example, Raman spectra of substances in water solutions exhibit the characteristic Raman fingerprints of both the substance and the water. For IR spectroscopy, the absorption of the water can be strong enough to completely obscure the IR spectrum of the substance, severely compromising chemical identification. The Raman fingerprint is also independent of the excitation wavelength, a feature unique to Raman spectroscopy that allows the use of any laser excitation wavelength. Hence, Raman detection can be performed in the ultraviolet (UV) solar-blind region of the spectrum ($\lambda$<300 nm, where stratospheric ozone absorption attenuates the solar background). Hence, detection can be done during the day, as well as at night, without the presence of a large background signal due to ambient light.

In addition to the advantages of solar-blind UV, the use of a UV source has several more distinct advantages. First, there is the $\nu^4$-dependence of the Raman scattering intensity on excitation frequency. The system sensitivity will increase by a factor of sixteen whenever the excitation frequency is doubled.

Second, there is a potential for improvement in the scattering cross-section through the phenomenon of pre-resonance or resonance-enhanced Raman scattering. As the excitation photon energy approaches that of an allowed electronic transition (as occurs in the UV for many chemical and biological species), an increase in the Raman scattering cross-section beyond the $\nu^4$-dependence is observed. This enhancement can approach several orders of magnitude. The combination of the $\nu^4$-dependence and the potential of pre-resonance or resonance indicates the overwhelming advantage of using UV excitation.

Third, the availability of low-noise optical multichannel analyzers in the visible and ultraviolet can permit capture of a large portion of the Raman spectrum. There is no need to scan the grating of the spectrometer to take a Raman fingerprint, eliminating the need for moving parts in the final instrument design.

Finally, the unique features of Raman spectroscopy make it a viable technique for detection of liquid or solid contamination on the ground or on man-made surfaces. Raman scattering can yield more information from a molecule on a surface than can absorption or fluorescence. In addition, Raman spectra can also yield quantitative information based on the intensity of the Raman signals.

Raman detection also offers the unique possibility of in situ discrimination of chemical and biological contamination. Experimental results suggest that Raman spectroscopy can detect and differentiate biological agents, even with regard to the phase of the substance in its lifecycle. This dual use of the UV Raman stand-off technique means that it could be used as a screening method for the selection of agent-specific, and thus more sensitive detectors.

Various devices have been disclosed which employ Raman spectroscopy to determine the constituents of substances. One such device is set forth in U.S. Pat. No. 5,257,085 to Ulich, et al., ("Ulich"). Ulich discloses an imaging UV/visible fluorosensing and Raman lidar system comprising an optical sensor for simultaneously measuring temporally, spatially and spectrally resolved laser backscatter from on land, on or beneath the surface bodies of waters and the atmosphere. The lidar system utilizes active or passive interrogation for remote and nondestructive probing of the spectrally-dependent optical properties of a scene. The Ulich device, however, is not a portable compact device which is suitable for use by first responders. The device requires a multitude of reflectors and prismatic elements which would be subject to alignment problems if used in a rugged environment. In addition, the laser beam and optical path of the telescope are not coaxial. Therefore, the laser beam is axially offset from the sight path of the telescope thereby reducing the ability to efficiently package the device.

U.S. Pat. No. 4,945,249 to Grant et al., ("Grant"), discloses an apparatus for detecting an anomaly at or near the surface of water or land. The apparatus includes a laser for generating a beam which is sufficiently intense that it causes the anomaly to emit secondary light radiation. The Grant device includes an intensified optical multi-channel detector, which is software configurable and capable of multi-element digitizing. The disclosed system is designed to be airborne and is not compact or portable, as would be required for use by emergency personnel. The system is not intended for short-range (i.e. meters to tens of meters) stand-off distances; consequently, the receiver telescope focus is unable to accommodate such changes in the object distance. Therefore, the device of Grant would not be suitable for in situ interrogation where the environment can present significant spatial constraints. In addition, the device is specifically designed to look for a known substance, i.e. fluorescence from oil seepage and employs a wavelength range, 300–800 nm, which is not in the solar blind region of the spectrum. This makes the device highly susceptible to errors caused by ambient lighting conditions.

Accordingly, it is desirable to provide a portable stand-off sensor which can perform remote, in situ, stand-off analysis of chemical/biological components and is configured such that it can be easily handled by emergency workers without the sensor being detrimentally affected. It would further be desirable to provide a method for remote, stand-off and highly efficient spectroscopic detection of solids, liquids, and gases.

SUMMARY OF THE INVENTION

The present invention provides a portable sensing apparatus for the remote interrogation of chemical or biological agents.

The present invention provides a sensing apparatus which permits standoff interrogation of a surface and is configured in a portable package such that the apparatus may be used in physically confined areas.

The present invention further provides an apparatus which includes an optical beam transmitter which transmits a beam comprising at least a pulsed laser emission having an axis of transmission. An optical detector is provided which gathers optical information and has an optical detection path to a target. The path has an axis of optical detection and the transmitter is disposed proximally to the optical detector. A beam alignment device is further provided which fixes the detector proximal to the transmitter and directs the beam to the target along the path such that the axis of transmission is within the path. Operatively connected to the detector is an analyzer for receipt of optical information and analysis of same.

The beam alignment device of the present invention may include a first beam-directing element for altering the axis of transmission of the beam. A second beam-directing element for altering the transmission axis of the beam may be further provided wherein the first beam-directing element directs the beam emitted from the laser at an angle such that the beam crosses into the optical direction path, and the second beam-directing element redirects the beam toward the target. The beam alignment device may also include a rigid structural element to fix the transmitter proximal to the detector.

The analyzer includes a spectrometer for creating a spectra by resolving scattered light energy by wavelength and a transducer for converting the spectra into electrical signals by way of a charged couple device.

In a preferred embodiment, the optical beam transmitter is a pulsed Nd:YAG laser having a wavelength in the solar blind region of the spectrum. Therefore, the sensing apparatus is not affected by ambient light conditions.

The present invention also includes a method for remote, stand-off, high speed and high efficiency spectroscopic detection of solids, liquids and gases, including the steps of:

establishing a co-linear optical transmission/detection path between, a combination optical beam transmitter and spectral analyzer and a target;

transmitting an optical detection beam comprising at least a pulsed laser transmission along the path to illuminate the target;

detecting optical behavior resulting from illumination of the target with the optical detection beam; and analyzing the optical behavior whereby characteristics of the target are detected.

A preferred form of the sensor, as well as other embodiments, features and advantages of this invention, will be apparent from the following detailed description of illustrative embodiments thereof, which is to be read in connection with the accompanying drawings.

Figure 1:
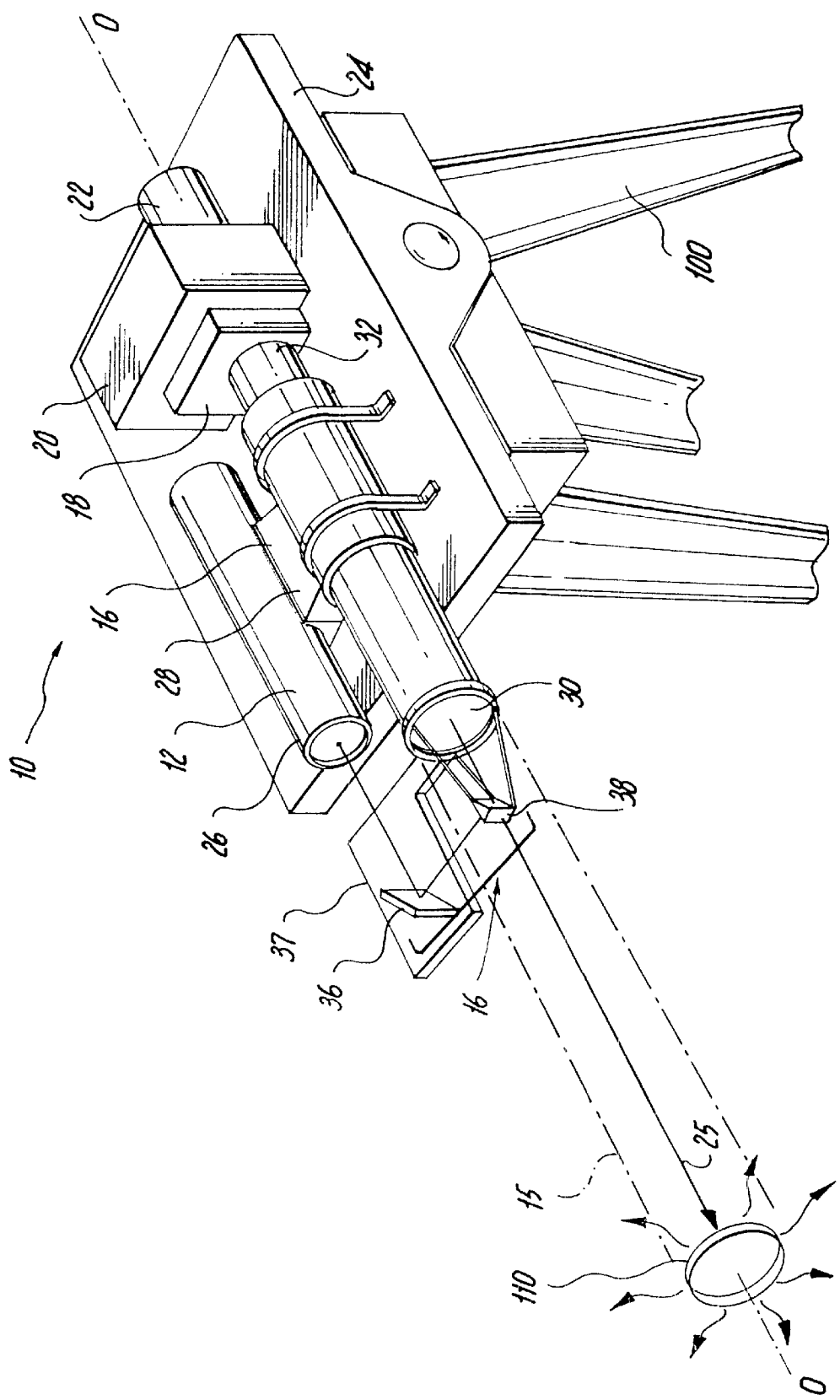
FIG. 1 is top perspective view of the mini-lidar sensor of the present invention.

FIG. 15 is a graphical representation of laboratory test results of a sensor of the present invention interrogating *B. thuringiensis,* and acetonitrile in aqueous solution.

DETAILED DESCRIPTION OF THE PREFERRED EMBODIMENT

The present invention provides a mini-lidar sensor, which is portable and compact, and therefore capable of being used for in situ detection and identification by those first to the scene in which the presence of a chemical or biological contaminant is suspected. The sensor is capable of detecting the presence of such contaminants or other agents in a remote, stand-off manner such that contact with the substance is not required. The sensor of the present invention is portable and efficiently designed such that it may be used in constricted areas such as in a subway or commercial or residential buildings.

The sensor employs Raman spectroscopy wherein an optical beam is directed toward a target in order to determine its composition. The target is illuminated by the optical beam and the resulting scattered light energy is collected. The collected in elastically scattered light is spectrally resolved and the wavelength shift of the scattered laser light with respect to the incident laser light is detected. The particular shift, or set of shifts, provides a unique fingerprint of the substance which is being interrogated, thereby permitting personnel to determine the agent's composition. The use of lidar equipment to employ Raman spectroscopy is known in the art; however, such devices in the past have not been acceptable for use by emergency personnel for in situ, stand-off interrogations due to the physical limitations of the prior art designs.

Stand-off detection using UV Raman spectroscopy offers the possibility of detecting and uniquely identifying a chemical or mixture of chemicals on a variety of surfaces, both natural and man-made. When fully developed, this technique will be vital to first responders at the scene of a terrorist attack or chemical spill. Stand-off Raman detection will allow them to quickly determine the severity and extent of chemical contamination without having to collect a sample or come into contact or near contact with the contaminants. For example, in the case of an attack involving VX, the agent has a low vapor pressure and is likely to leave a residue on the ground, on cars, and on buildings. Stand-off Raman detectors can quickly survey a number of surfaces to determine the identity of the substance and to perform contamination mapping at whatever spatial resolution is appropriate. Contamination mapping is an important task for tracking the spread of a chemical substance as well as aiding in decontamination efforts.

Now referring to the drawings, FIG. 1 is a schematic illustration of the mini-lidar sensor of the present invention. Sensor 10 generally preferably includes an optical beam transmitter 12, an optical detector 14, a beam alignment device 16, an optical filter 18, a spectrometer 20, and detector 22. Each of these components may be compactly configured on a support platform 24.

Sensor 10 is preferably a compact unit having a footprint of approximately 18"×30" with a height of 42". These dimensions are illustrative and not intended to be limiting. It is within the contemplation of the present invention that the footprint could be significantly reduced depending on the reduction in size of the individual components. Such a relatively small footprint permits the unit to be portable and transported by "first responders", i.e., those individuals first on the scene in an emergency situation, and permits sensor 10 to be used in physically constrained environments. Sensor 10 is portable to the extent that it can be transported and operated by a two-person team. The compactness of the design also adds to the ruggedness of the sensor, which is required for field use of emergency type of equipment. Accordingly, sensor 10 is well suited for use by emergency personnel in situations where chemical/biological contaminants have been either intentionally or accidentally introduced to inhabited areas and the nature and extent of the contamination must be rapidly assessed.

Sensor 10 permits remote interrogation of agents and can effectively operate at distances up to tens of meters. The operative range of sensor 10 is approximately 2 m to 50 m. No part of sensor 10 is required to contact the substance being interrogated at any time. Furthermore, the operator of the device and the sensor itself may be located some distance from the material and may even be located behind a protective transparent shield. This feature is highly desirable since certain agents may be extremely hazardous and any contact therewith could result in bodily harm to the sensor operator.

The efficiency of the design and the ability to package sensor 10 to provide the portability and ruggedness in design, is achievable in significant part due to the sensor's alignment of the optical viewing path of optical detector 14 with the transmission path of the beam created by the beam transmitter 12 by way of a beam alignment device 16. Specifically, the transmission path of the beam is directed to be within the optical path 15 of optical detector 14. In a preferred embodiment, the transmission path of the beam is substantially coaxial with the central axis O—O of the optical path 15 of optical detector 14, as shown in FIG. 1. However, it is within the contemplation of the present invention that the beam may be axial offset from the central axis of optical path 15 (FIG. 2) and aligned essentially anywhere within the optical path of optical detector 14 such that the scattered light energy may be collected by same in order to perform the analysis.

In one embodiment, optical beam transmitter 12 may include a laser which emits a pulsed laser beam 25. Lasers are particularly useful to produce Raman scattering at a distance due to the emitted beam's spectral purity, high photon flux, and high degree of collimation. Laser 10 may include a commercially available 266 nm Nd:YAG laser having transmitting optics located on a transmitting end 26. The present invention also contemplates the use of a continuous wave, CW, laser. Laser 12 should preferably produce a beam having a wavelength that generates Raman scattered wavelengths within the solar blind spectral region (<300 nm). By employing such a wavelength, no compensation is necessary for the effects of ambient solar radiance and ground albedo. However, other wavelengths may be used, including those in the visible range, as long as the effects of ambient light are compensated for. Laser 12 is preferably capable of producing a pulsed beam of energy which is directed toward a target. Laser 12 may be remotely powered by a dedicated generator capable of producing approximately 1000 watts of electrical power. Other power sources may be used as it known in the art.

In an alternative embodiment, laser 12 may be an infrared diode type laser. While infrared does not produce the same intensity of Raman scattered photons as UV lasers, diode lasers are typically physically smaller and require significantly less power than flashlamp-pumped Nd:YAG lasers.

The light energy transmitted by laser beam 25 illuminates the target substance and is scattered by a target 110 to produce Raman scattered photons. These photons are gathered by the receiving end 30 of optical detector 14. Optical detector 14 has a predetermined field of view and an optical detection path 15 which is aligned with the target. An axis of optical detection O—O extends along the center of path 15. Optical detector 14 may comprise a telescope which is positioned adjacent laser 12 and secured thereto. Various types of telescopes may be used including reflecting or refracting telescopes. One such telescope which has been found to be suitable is a 5-inch Cassegrain telescope with an adjustable focus.

In order to bring the transmission path of laser beam 25 into alignment with the optical detection path 15 of telescope 14, a beam alignment device 18 is provided. Beam alignment device 16 structurally fixes optical beam transmitter 12 proximal to optical detector 14 and effects the alignment of laser beam 25 to achieve the desired transmission path. A structural connection between optical beam transmitter 12 and optical detector 14 may include a mounting bracket 28 which extends between the two elements fixing them adjacent to each other. Beam alignment device may further include a first beam director which is preferably a reflector 36. Reflector 36 directs laser beam 25 as transmitted from laser 12 at a 90° angle toward and into the optical detection path 15 of telescope 14 as shown in FIG. 1. Reflector 36 may be formed of a glass mirror device or a highly polished metallic surface. Precision mirrors having a reflectance of approximately 99.9% have been found to be particularly suitable. While the position of reflector 36 is preferably fixed, an adjustment device (not shown) may be included in order to permit realignment of reflector 36 to control the direction of laser beam 25. Reflector 36 may be attached to telescope receiving end 30 by a plate 37. Plate 37 extends radially outward from telescope 14 toward the transmission path of beam 25. Reflector 36 may then be disposed on an outer end of plate 37 such that reflector 36 intersects the transmission path of beam 25 and directs same.

Figure 2:
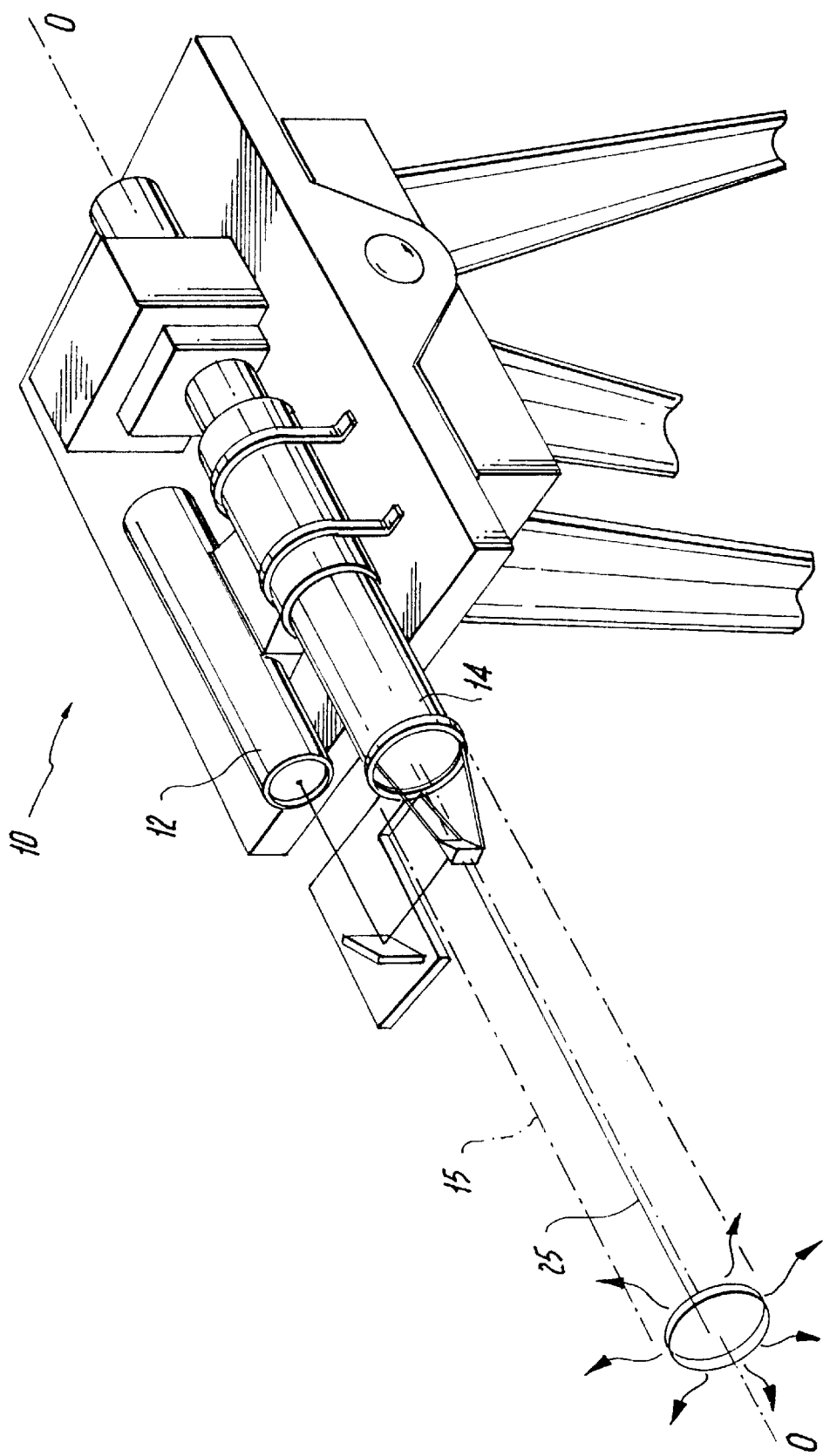
FIG. 2 is a top perspective view of the sensor of FIG. 1 showing a beam transmission radially offset from an axis of optical detection.

Beam alignment device 16 may further include a second beam director which is preferably a prismatic element 38. Prismatic element 38 redirects the reflected laser beam 25 at substantially a right angle toward target 110. Prismatic element 38 is preferably positioned in the center of the field of view of telescope 12 such that the redirection of beam 25 results in the beam being axially aligned with the central axis O of the optical detection path 15 as shown in FIG. 1. Thus, a co-linear optical transmission/detection path is established. By substantially axially aligning beam 25 with the central axis O—O of the optical detection path, telescope 14 is capable of collecting the maximum amount of scattered photons which radiate outwardly from the beam impact point on the target. Although not optimal, in an alternative embodiment shown in FIG. 2, laser beam 25 may be within the optical path of telescope 14, but may be axially offset from the central axis O—O of the optical path as shown in FIG. 2. However, in order for the scattered protons to be properly detected, the redirected laser beam transmission path should fall within the field of view of telescope 14.

The alignment of beam 25 within the optical path of telescope 14 and the proximal connection between laser 12 and telescope 14 permits sensor 10 to be more compactly designed than those prior art sensors which direct a laser beam along a transmission path which is outside the optical direction path of an optical detector. In such instruments the optical detector and beam transmitter are typically spaced from each other at an angle. Therefore, the optical path of the optical detector and transmission path of the beam only intersect at the target. Sensors of this prior art designs are not packagable in a portable design and also require relatively complex aiming apparatus to insure that the transmission path of the beam and optical path of the optical detector intersect adjacent the target. In addition, various prior art sensors tend to space the optical detector apart from the optical transmitter leading to inefficient designs which are not suitable for portable devices.

In the present invention, when laser beam 25 strikes the surface target which is to be interrogated, laser light is scattered and reflected back toward telescope 14. Telescope 14 collects the scattered photons in telescope receiving end 30 and concentrates the light energy which is emitted from telescope output end 32. As set forth above, the scattered light is both elastic and inelastic in nature with the elastic scatter dominating. The strength of the strong elastically scattered return compared to the faint inelastic Raman scatter, which is used to determine the composition of the target, is beyond the dynamic range of commercially available optical array detectors. Elastically scattered light is preferably rejected by use of an optical filter 18 positioned directly adjacent telescope output end 32. Filter 18 preferably includes a commercially available sharp-cut interference filter. Filter 18 permits the transmission of inelastic scatter so that it may be processed to determine target composition. In an alternative embodiment, filter 18 may include a single stage grating spectrometer which acts as a predisperser for rejecting the elastically scattered light. The predisperser rejects the elastically scattered light and permits the passage of in elastically scattered light, which is employed in Raman spectroscopy.

The light energy transmitted through filter 18 is then processed by a spectrum resolving device such as a spectrometer 20. A variety of spectrometers may be employed. The light energy enters an input slit of spectrometer 20 which is adjacently disposed to filter 18, and is resolved into its various component wavelengths forming a spectra in a manner well known in the art.

The output of spectrometer 20 are bands of faint light which contain the information which can be analyzed to determine the composition of the target. In order to convert the optical information into electronic signals for processing, sensor 10 may further include a detector transducer 22. Detector transducer 22 is preferably an intensified charged couple device, ICCD, which has a high degree of sensitivity to light. The ICCD converts the light energy into electronic signals which may then be processed by a computer device. Alternatively, a low noise CCD detector may be employed. The telescope 14, filter 18, spectrometer 20 and ICCD detector 22 are all aligned in a row as shown in FIG. 1, resulting in a compact design.

Figure 10:
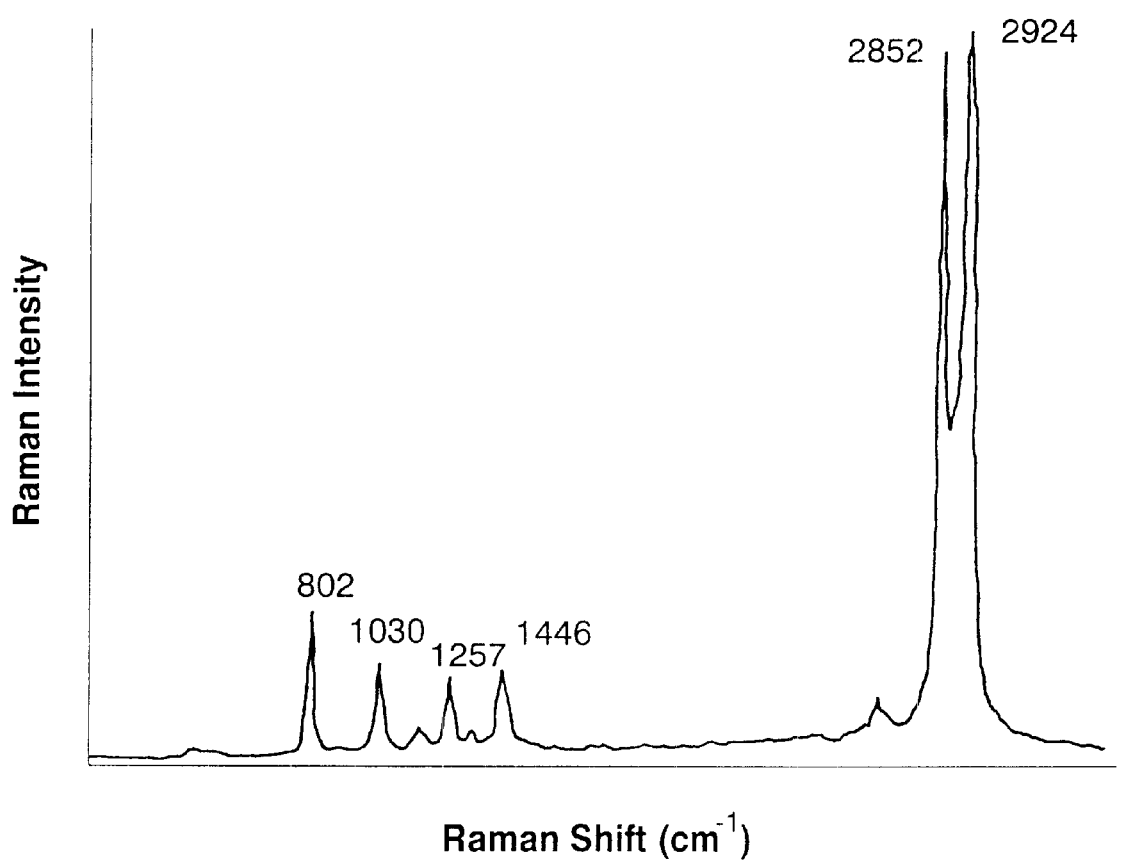
FIG. 10 is a graphical representation of laboratory test results of the sensor of the present invention interrogating cyclohexane.

The information received by the ICCD is then preferably fed to a micro computer where the information is processed in order to indicate to the users the composition of the target agents being interrogated. The information collected by sensor 10 can then be outputted in the form of a graph as shown in FIG. 10. The Raman return intensity forms the Y axis which is the sum of light signals falling onto a particular vertically aligned column of pixels of the ICCD. The shift of Raman lines with respect to the laser excitation forms the X axis. The Raman shift is labeled in frequency units known as wavenumbers, or inverse centimeters ($cm^{-1}$), wherein the conversion between wavelength and wavenumbers is $v=1/$. Each Raman-activated molecule has its own unique Raman fingerprint; therefore, the information collected can be compared either manually or via a micro processor to the data of known compounds such that the sensor can accurately determine the composition of the substance that is being interrogated. For example, a micro processor, such as a portable laptop computer could be programmed to interpret the output of the ICCD and display the chemical or biological composition and concentration of the target substance. The displayed information would be easily comprehended by an emergency worker, with little or no scientific background. Based on the results of the scan, appropriate measures could be taken to contain the contamination and insolate the affected area.

The various components forming sensor 10 are securely mounted to a rigid platform 24. This ensures that the alignment of the components is preserved as the pointing direction changes. The pointing agility of sensor 10 makes the device especially suited for contamination mapping in confined environments. Platform 24 may be mounted to a commercially available tripod 100. Tripod 100 may have a two axes swivel head and a height adjustment to permit sensor 10 to be aimed like a camera at the target. By mounting all of the components to rigid platform 24, sensor 10 may by easily transported and positionally adjusted for aiming purposes.

Figure 3:
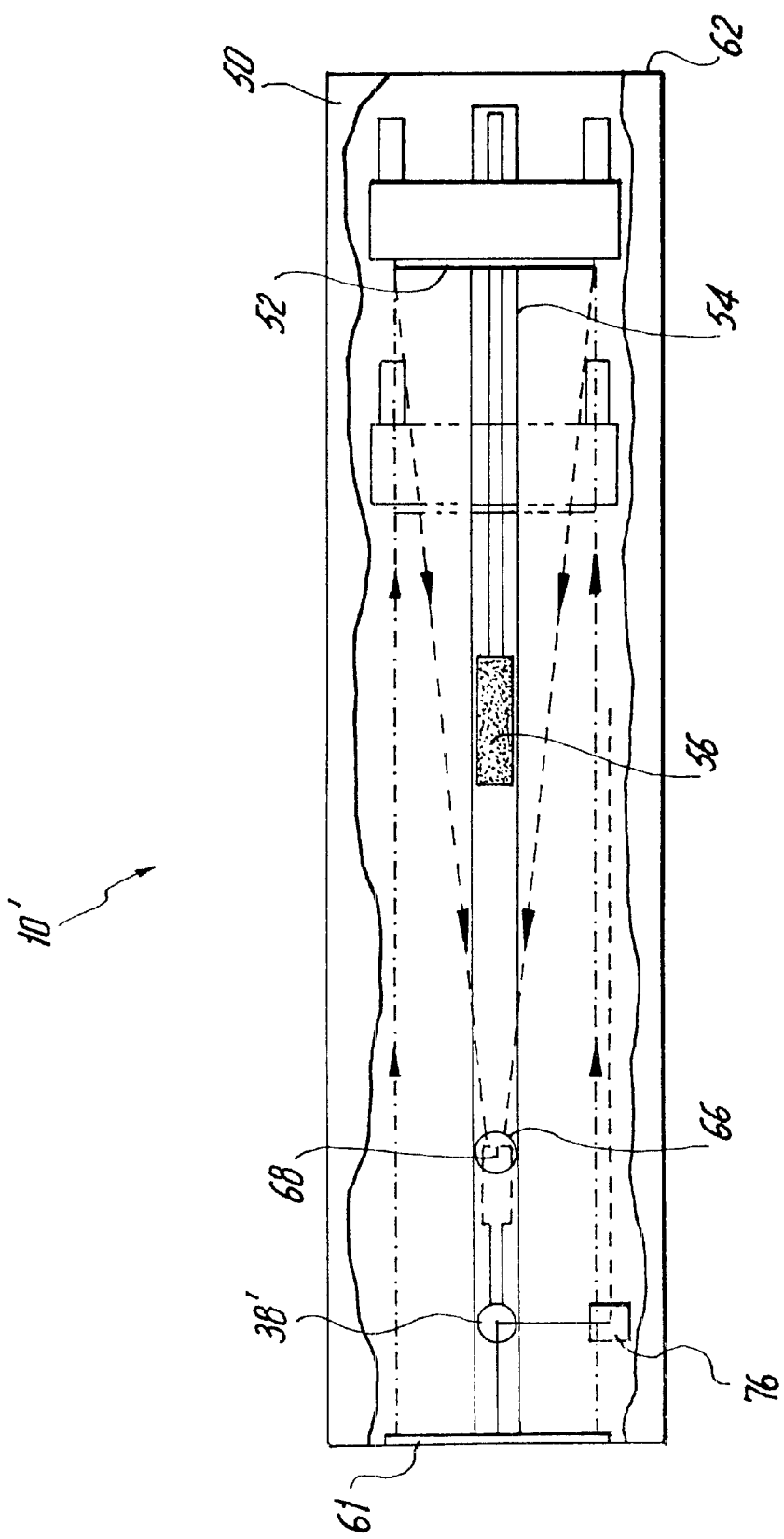
FIG. 3 is a top plan view of the preferred embodiment of the mini-lidar sensor of the present invention.
Figure 4:
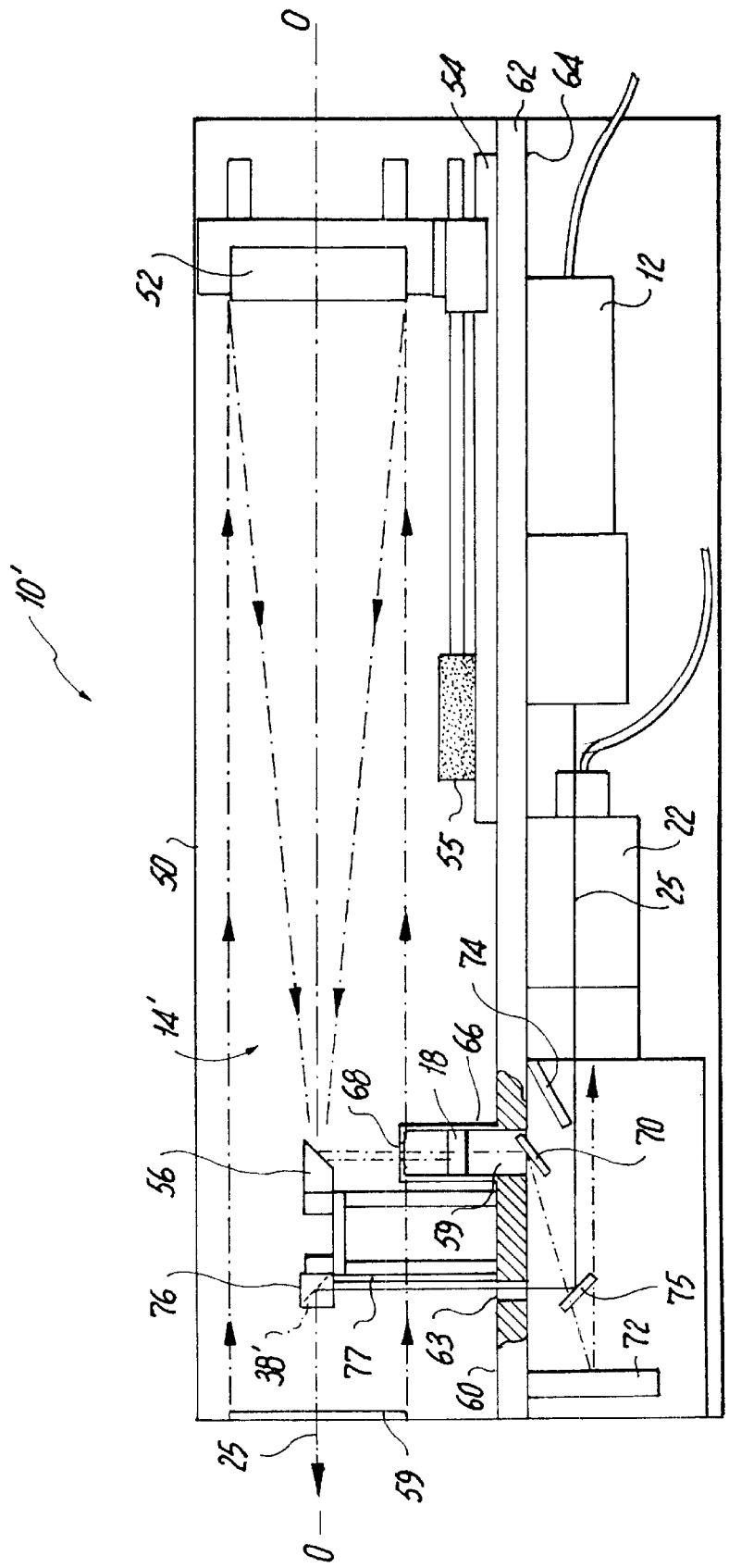
FIG. 4 is a side elevational view of the sensor of FIG. 3.
Figure 5:
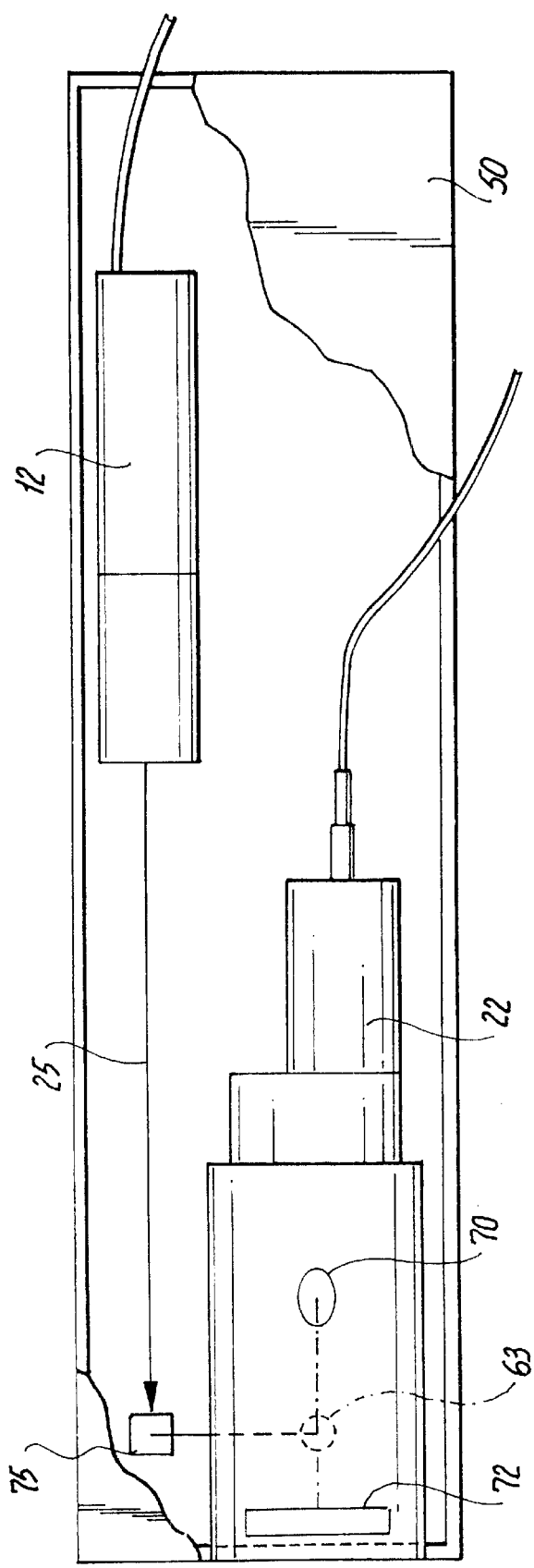
FIG. 5 is a bottom elevational view of the sensor of FIG. 3.

In a preferred embodiment, shown in FIGS. 3 to 5, sensor 10' may include a housing 50 which surrounds and protects the various components from contamination. Optical detector 14' is preferably a reflecting-type Newtonian telescope having a primary mirror 52 mounted to a linear guide 54. Linear guide 54 permits the position of primary mirror 52 to be adjusted to allow focusing of the telescope. Linear guide 54 is preferably a ball-screw type drive mechanism which is operated by a remotely controlled DC motor 55. A secondary mirror 56 is provided and positioned toward the front end of housing 50. Primary mirror 52 is preferably substantially 6 inches in diameter and the secondary mirror is substantially 0.75 inches in diameter. The mirrors 52 and 56 may be of a variety of sizes in order to obtain the desired magnification. An aperture 59 covered by a transparent window 61 is formed in housing 50 to permit light to enter the telescope.

In the preferred embodiment, in order to further reduce the footprint of sensor 10', the various components forming the sensor may be mounted on the top and bottom surface of a rigid platform. Specifically, optical detector 14' may be mounted on the top surface 60 of a platform 62. In this preferred embodiment, optical beam transmitter 12 and ICCD 22 are mounted on a bottom surface 64 of platform 62.

The light energy which enters window 61 is reflected by the primary mirror and directed toward the secondary mirror. Secondary mirror 56 is positioned at an angle to direct the light at a 90-degree angle toward a cylinder 66 having a slit 68 formed in the top thereof Light passing through slit 68 then encounters filter 18 disposed with cylinder 66. Filter 18 may include a sharp cut interference filter which rejects the elastically scattered light and permits transmission of the in elastically scattered light. An aperture 63 in platform 62 permits the filtered light to project therethrough. The filtered light is then directed by a reflector 70 toward a concave grating 72. Grating 72 creates a spectra from the colliminated light passing through slit 68. ICCD 22 is positioned in front of grating 72 such that the spectra formed thereon can be viewed. In order to ensure that the ICCD does not have a line of sight to the light passing from slit 68 to grating 72, a light baffle 74 may be included. This ensures that the ICCD only senses the spectrum formed by grating 72.

As in the previous embodiment, the axis of transmission of laser 12 is preferably co-linear with the axis of optical detection O—O of telescope 14'. Therefore, similar to the previously described embodiment, the preferred embodiment also includes a beam alignment device. Beam alignment device 16' includes a series of mirrors and a turning prism, which brings the beam up through platform 62 and into co-linear alignment with the axis of optical detection O—O. Specifically, beam 25 emitted from laser 12 is first strikes a mirror 75 having a high reflectance and directs the beam 90 degrees up through an aperture 63 in platform 62. The directed beam 25 then engages a second angled mirror 76 which redirects beam 25 toward turning prism 38'. Turning prism then directs beam 25 toward the target on a path co-linear with the axis of optical detection O—O. Second mirror 76 is preferably supported above platform 62 at the same level as turning prism 38' by a thin rod 77.

Sensor 10' may be removably fixed to a stand such as a tripod to permit pointing of the sensor toward a target.

Figure 6:
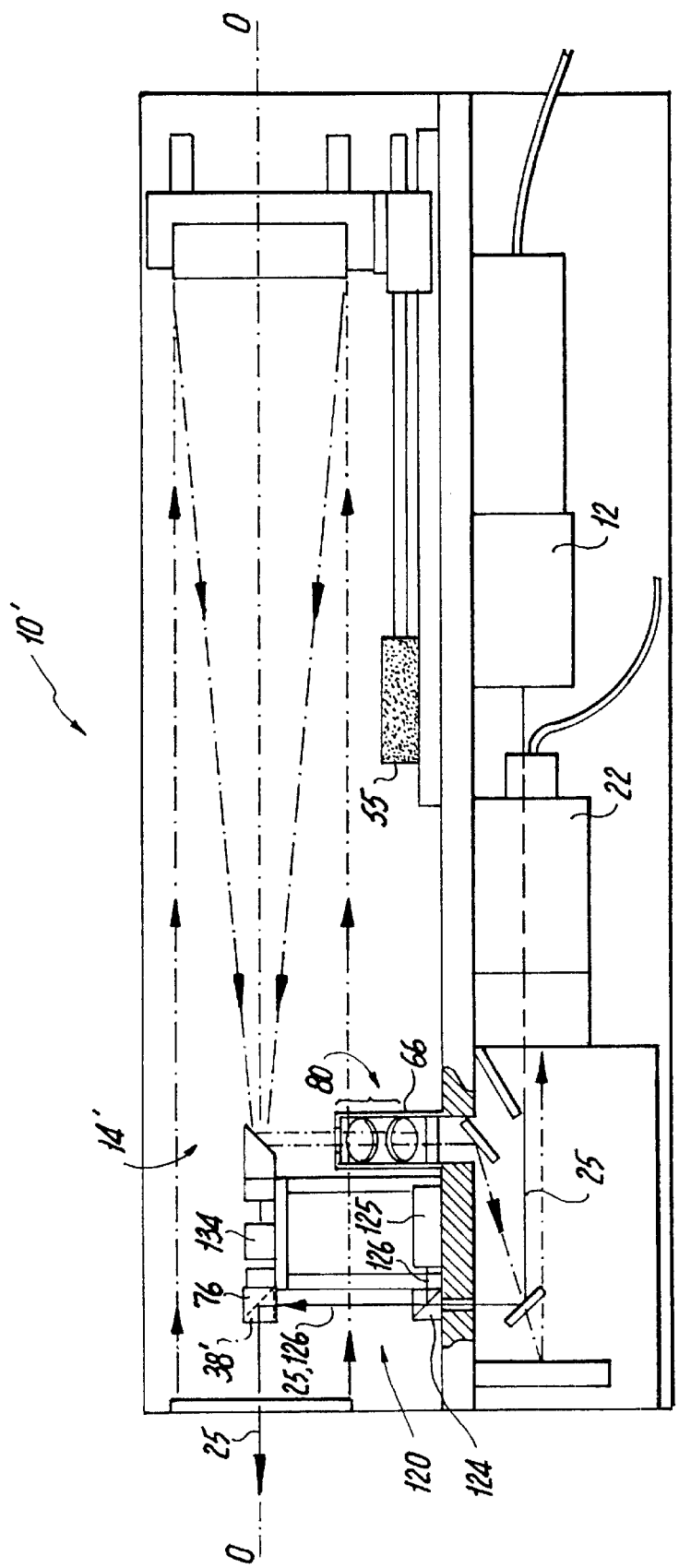
FIG. 6 is a side elevational view of an alternative embodiment of the present invention including a screening apparatus and auto-focusing device.
Figure 7:
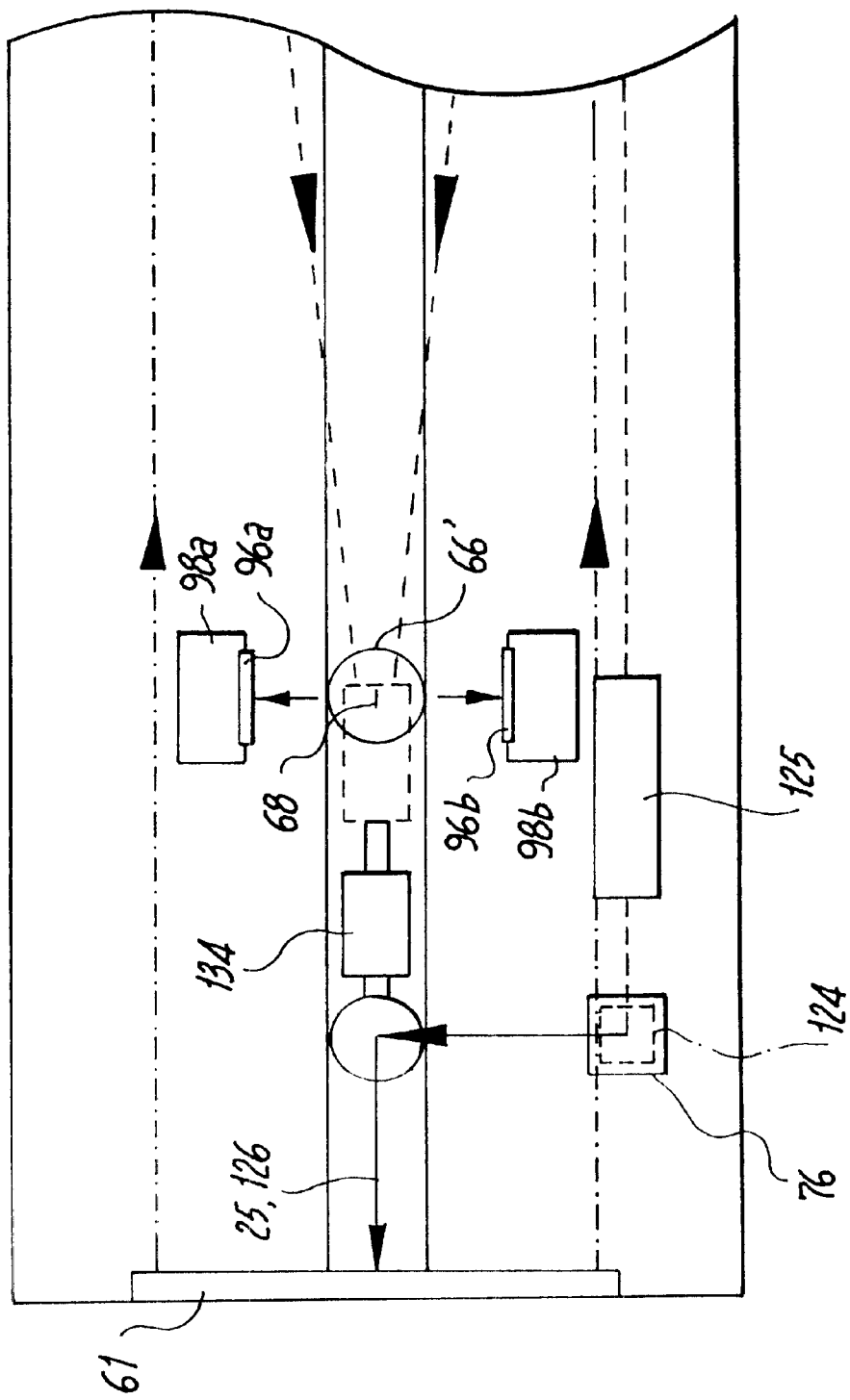
FIG. 7 is a partial top plan view of the sensor of FIG. 6.

In order to focus sensor 10' on the target, an autofocusing apparatus may be included and operatively connected to motor 55 to adjust the position of primary mirror 52. The autofocusing apparatus could include a laser range finder which would determine the distance to the target. This information would be processed and a signal would then be given to motor 55 to adjust the position of primary mirror 52. In a preferred embodiment shown in FIGS. 6–8, laser range finder 120 includes a polarizing beam splitter 124. Beam splitter 124 may be in the form of a quartz block formed from two Brewster-angle prisms joined together positioned over platform aperture 63. The polarization of laser beam 25 is such that it passes straight through beam splitter 124. A range-finder beam generator 125 is mounted on the top side of platform 62 adjacent beam splitter 124. Range finder beam generator 125 produces a laser range-finder beam 126 which is directed toward beam splitter 124. The polarization of laser range-finder beam 126 is orthogonal to that of laser beam 25 used for probing the target. Therefore, beam 126 undergoes internal reflection off the inside surface of the polarizing beam splitter 124. The two laser beams 25 and 126 exit the beam splitter 124 collinear, reflect off second mirror 76, pass through turning prism 38' and exit sensor 10' collinearly. Second mirror 76 preferably includes a dual high reflectance coating for both laser beams 25 and 126.

Figure 8:
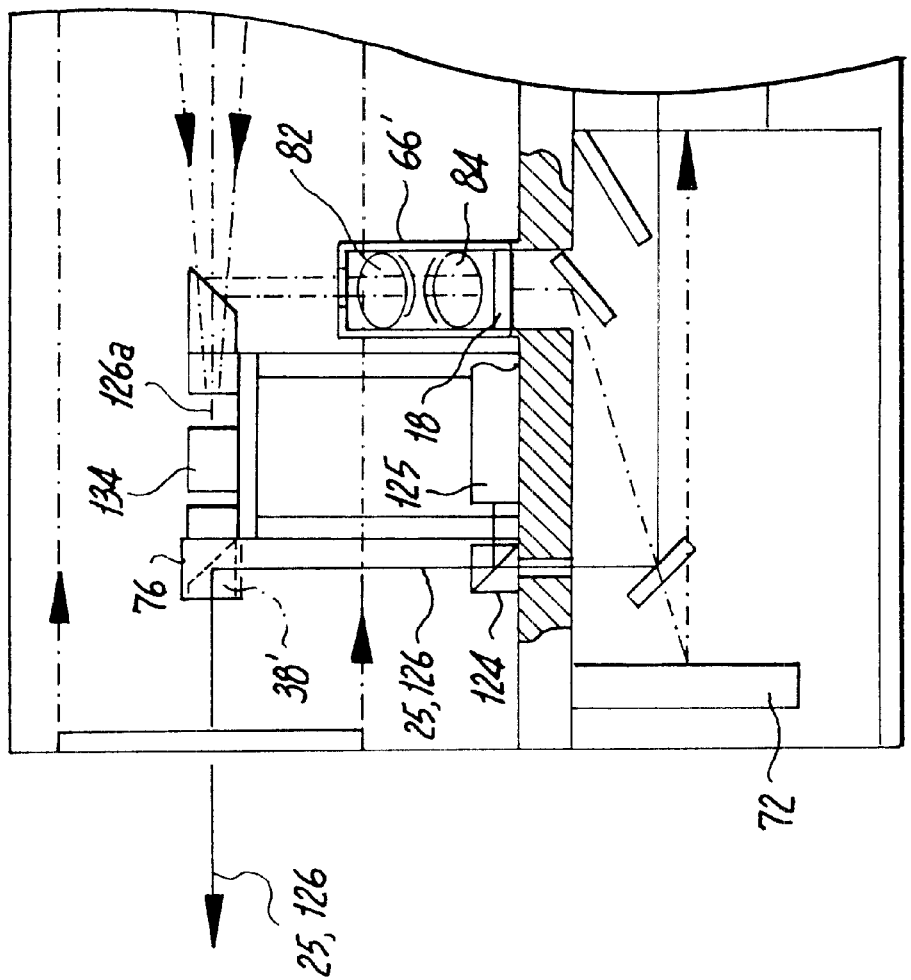
FIG. 8 is a partial side elevational view of the sensor of FIG. 6.

The laser light of both laser beams 25 and 126 is reflected from target 110 and collected by telescope 14'. Secondary mirror 56' is coated such that it reflects the wavelength of laser beam 25 and Raman wavelengths and transmits the wavelength of the laser range-finder beam 126, as shown in FIG. 8. Secondary mirror 56' is fixed to a mount 130 which includes a small aperture 132 extending therethrough. Aperture 132 permits the light collected from the laser range-finder beam 126 to pass through and fall upon a photodiode 134 positioned adjacent secondary mirror 56'. Photodiode 134 measures the signal and determines the range to the target. In addition, laser range-finder beam 126 is preferably visible to assist the operator to locate the pointing direction of the sensor.

In a further alternative embodiment, sensor 10' may include a screening apparatus 80 for quickly scanning a surface to detect the presence of contamination. Once contamination is detected, sensor 10' can scan the suspect areas more slowly in order to obtain a Raman spectrum and thus identify the contaminant(s).

Figure 9:
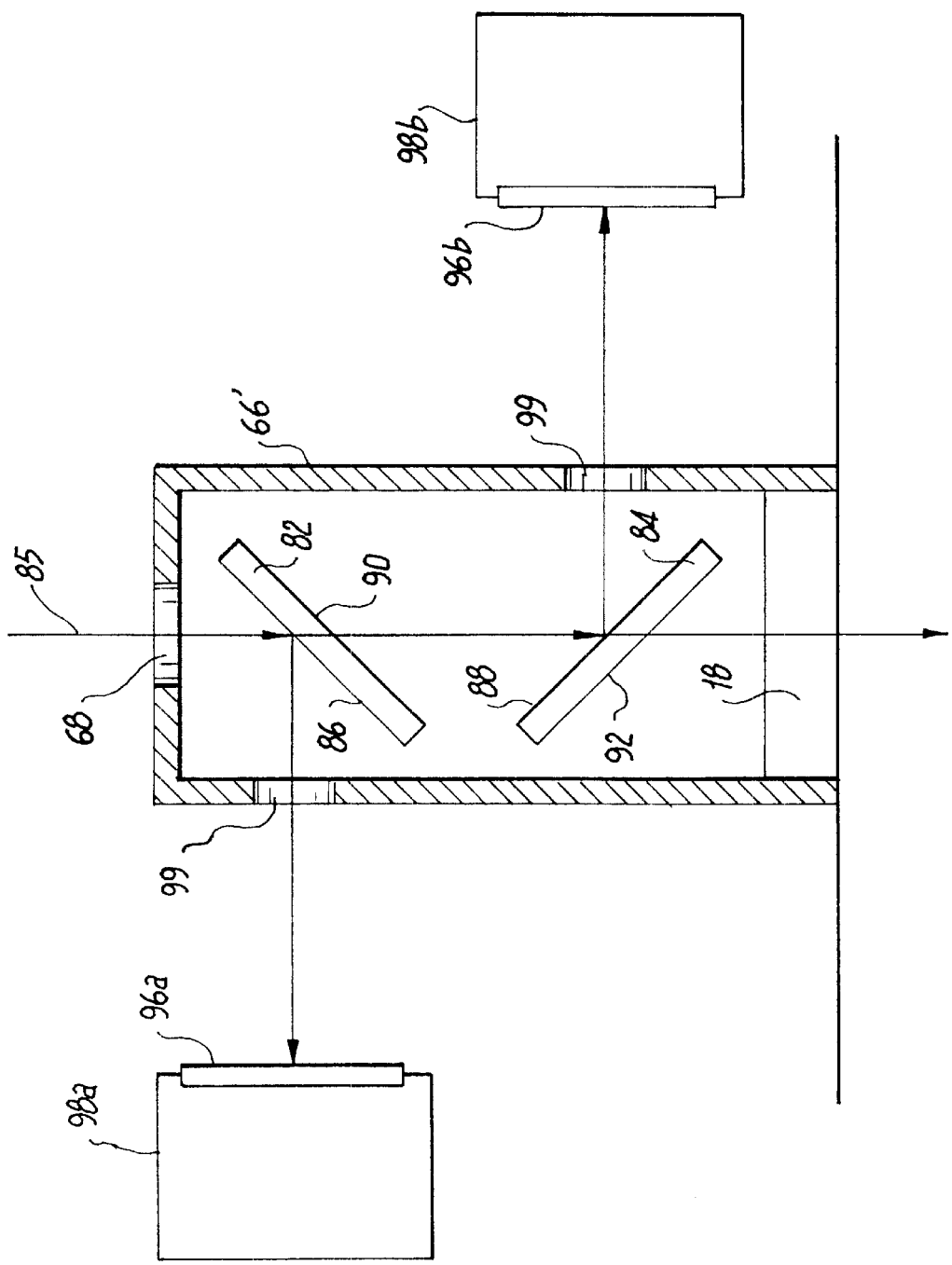
FIG. 9 is a side elevational detail view of the screening apparatus of FIG. 6.

Referring again to FIGS. 6–9, to quickly detect contamination, screening apparatus 80 of sensor 10' relies on changes in the polarization of the elastically scattered laser light. The laser light incident on the surface is linearly polarized. Hence, the elastically scattered light will contain components in orthogonal states of linear polarization, known as the S and P polarization states. The S and P states are analyzed by placing a first 82 and second 84 transparent optical flats into the receiver beam path 85 just before filter 18 which rejects the elastically scattered light filter. Referring specifically to FIG. 9, the upper surface 86 of first flat 82 and the upper surface 88 of second flat 84 are uncoated, while the lower surface of the first and second flat, 90 and 92 respectively, has an anti-reflection coating for the laser wavelength. The angles of the first and second flats 82, 84 with respect to the axis of the receiver beam path are +45 degrees and −45 degrees, respectively. This ensures that beam displacement due to first flat 82 is compensated by second flat 84. First and second flats 82 and 84 may be supported in cylinder 66' above filter 18. Cylinder 66' includes a pair of diametrically opposed channels 99 which are aligned with an axis of reflection of the first and second flats 82, 84. The light directed by secondary mirror 56 passes through slit 68 and is reflected from each of the uncoated upper surfaces 86 and 88 is passed through a pair of polarization analyzers 96a and 96b, one for measuring S polarization and the other for measuring P polarization. A pair of photomultiplier tubes 98a and 98b measures the transmission through the respective polarization analyzers. The ratio of S polarization to P polarization of the elastic backscatter is monitored as the laser beam from sensor 10 scans across a surface. A change in the ratio suggests the presence of a contaminant that has changed the optical properties of the elastic backscatter. Once such an area is identified, a scan may begin to determine the composition of the contaminant.

The present invention further contemplates using the total backscatter signal (the sum of the S and P polarizations) as a monitor of aerosol density. In this mode of operation, sensor 10' is scanning the air above a surface and obtaining, through the two photomultiplier tubes, the total elastic backscatter as a finction of distance from sensor 10'. This data can be used to estimate the aerosol size and density. It has been found that the use of several different laser wavelengths, which is a possibility for a Nd:YAG laser, provides a better estimate of aerosol particle size. Finally, the combination of aerosol size and density above a surface provides an estimate of surface coverage from the settling of the aerosol particles on the surface.

In operation, sensor 10 could be carried to a scene of suspected contamination by two individuals. The sensor may be set up within the operational range of the device which is approximately 2 m to 50 m. Once the sensor is connected to a power source, an operator would aim the telescope 14 such that the optical direction path aligns with the target to be interrogated. The energizing of laser 12 results in the transmission of a beam 25 having a wavelength in the solar blind region. The transmission path of beam 25 is altered upon engagement of reflector 36 and prismatic element 38 such that it is substantially coaxially aligned with the optical direction path of telescope 14. Therefore, the axis of transmission of laser 12 is co-linear with axis optical detection O—O. Telescope 14 may be focused to adjust for the distance between the sensor and the target. The scattered photons are then collected by telescope 14 and the elastically scattered photons are removed by filter 18. The inelastically scattered photons are passed through filter 18 and spectrally resolved by spectrometer 20. The optical information is captured by ICCD 22 and converted to electrical signals which are analyzed by a microcomputer. Scanning of a target is completed within 2 to 5 minutes with the output being relayed to an operator.

The operation of sensor 10' is essentially the same as for sensor 10 described above. In addition, a screening apparatus 80 may be employed to first make a quick scan of a surface to determine if the surface is covered by a substance. Once this is determined, the operator can then begin a Raman interrogation of the surface to determine the make-up of the substance.

The sensor of the present invention can also be used to perform in situ stand off detection and identification of biological materials including bio-chemicals as well as whole cells on surfaces. As with chemical substances, it has been found that molecules forming biological material produce a unique Raman signature that is capable of being identified upon interrogating a contaminated surface. In order to interrogate biological substances, sensor 10 preferably is equipped with a laser capable of transmitting a beam having a wavelength of approximately 244–250 nm. Such a wavelength works well for detecting both chemical and biological substances. A wavelength of 248 nm is believed to be particularly well suited for the detection of biological as well as chemical substances. This wavelengths in this range result in a fluorescence-free Raman spectral window. However, it is believed that wavelengths ranging from approximately 229–280 nm would provide acceptable results. The Raman signal from the biological materials is shifted to the blue of the strong fluorescence from many bio-molecules. The use of a UV laser, rather than a visible laser, is preferred because of the near resonance enhancement in the Raman signal cross-sections.

Figure 14:
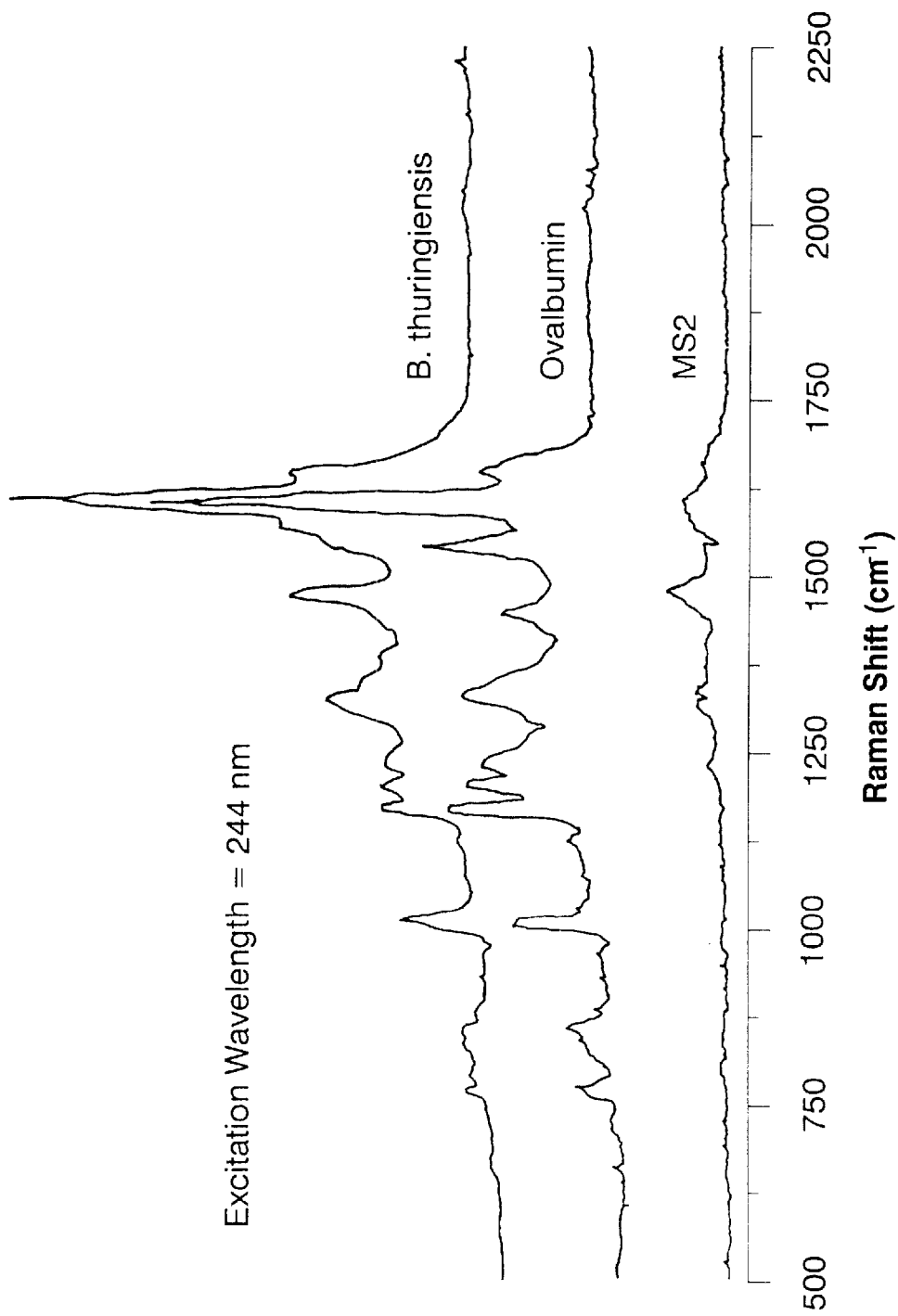
FIG. 14 is a graphical representation of laboratory test results of a sensor of the present invention interrogating biological substances *B. thuringiensis,* Ovalbumin and MS2.

The ability of a sensor employing a Raman based system for the detection and identification of biological materials is illustrated in FIG. 14. Under laboratory conditions, whole cells of a strain of bacteria, Bacillus thurgiensis, was a interrogated by a laser having a wavelength of 244 nm resulting in the detection of a Raman shift. A bio-molecule ovalbumin or egg white and a virus MS2 were also interrogated producing unique Raman shifts. In addition the portable stand off sensor 10 of the present invention has been shown to be effective in the standoff detection of biological substances. Furthermore, as set forth in the Examples below, sensor 10 has been shown to be effective in the detection of and discrimination between both biological and chemical substances.

EXAMPLES

Laboratory and field testing of the sensor of the present invention have demonstrated its operational effectiveness as a remote sensing device for determining the composition of a target substance.

The sensor employed during the laboratory testing consisted of a pulsed 266 nm Nd:YAG laser (20 Hz, 7 mJ/pulse) and a 5-inch diameter Cassegrain telescope. The axis of transmission of the beam produced by the laser was co-linear with the axis of optical detection of the telescope. A filter to reject elastically scattered light included a sharp-cut interference filter. A single stage 0.25 m spectrometer with a 2380 groove/mm grating blazed for 250 nm served as a spectral resolver for the Raman light. A 18 mm wide CCD detector with intensifier captured a 3500 $cm^{-1}$ wide portion of the Raman spectrum. (It is typical within the art to express the positions of lines of a Raman spectrum in terms of their shift in frequency relative to the laser excitation frequency, rather than in terms of their absolute wavelength. The frequency units of the Raman shift are inverse centimeters ($cm^{-1}$), where 1 $cm^{-1}$ equals 30 GHz). Data acquisition and analysis were controlled by a laptop computer.

This sensor configuration as set forth above was used to interrogate cyclohexane in a 10-mm quartz cell. The integration time was 5 seconds, and the stand-off distance was 2 m. The results of the scan are graphically set forth in the FIG. 10.

Figure 11:
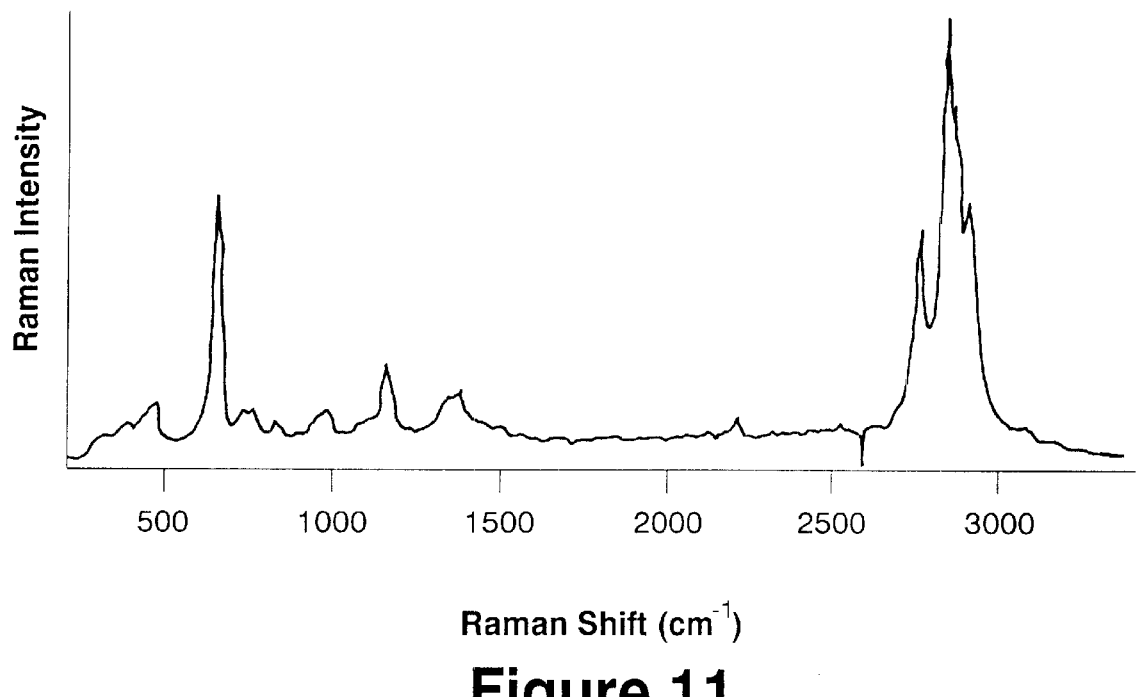
FIG. 11 is a graphical representation of laboratory test results of the sensor of the present invention interrogating DMMP (dimethyl methylphosphonate).

Further tests were conducted with the set up as described above except a Newtonian telescope replaced the Cassegrain telescope. This set up was used to interrogate DMMP (dimethyl methylphosphonate) in a 10 mm cell. The integration time was 1 minute and the stand-off distance was 2 m. The result of the scan is graphically set forth in FIG. 11.

Figure 12:
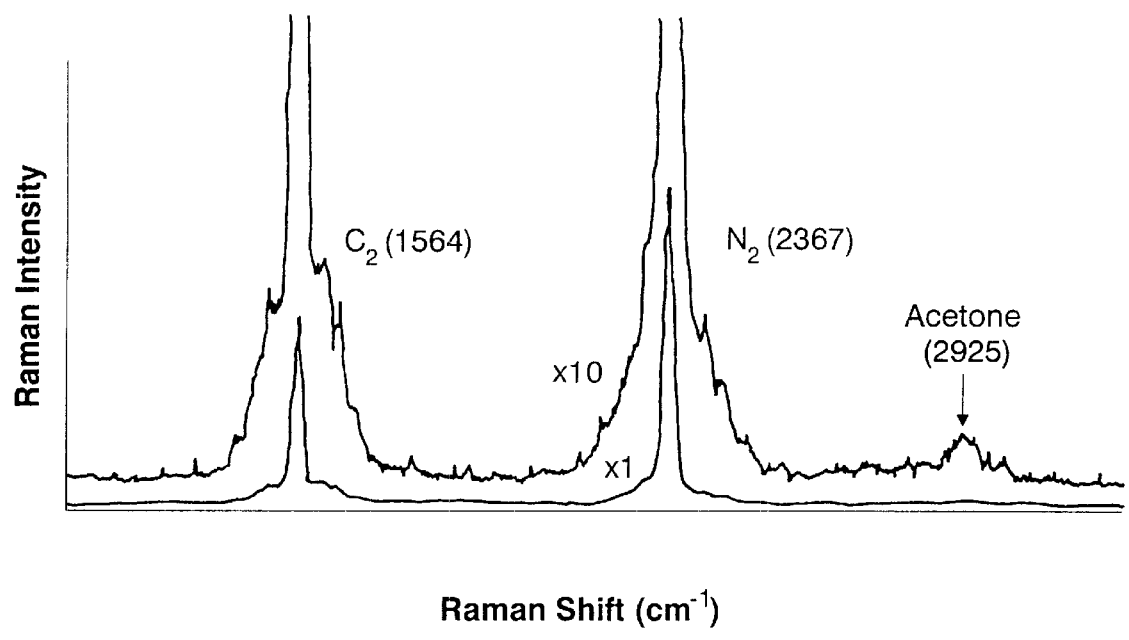
FIG. 12 is a graphical representation of field test results of the sensor of the present invention interrogating acetone on a felt cloth.

A field test of the sensor of the present invention was conducted employing a sensor as described above with the Cassegrain telescope. In addition, instead of the sharp cut filter a single-stage 74 mm grating spectrometer (known as a "predisperser") with a 2400 groove/mm grating blazed for 250 nm was used to reject the elastic scatter. The entrance slit size of the predisperser was 100 microns, and a 2 mm exit slit served as a mechanical knife edge. The width of the spectral window was 1500 $cm^{-1}$ due to the 2 mm width of the exit slit. The surrogate chemical for the exercise was acetone, which was poured onto a black felt cloth and placed five meters from the sensor during a rainstorm. The results of the scan after 8 minutes of integration are shown in FIG. 12. (Numbers in parentheses indicate Raman shifts in $cm^{-1}$) FIG. 12 shows the Raman line due to the C-H stretching mode of acetone, as well as the modes of atmospheric nitrogen and oxygen. The test was conducted during a rain storm and the presence of water did not obscure the Raman modes. The modes of $N_2$ and $O_2$ are an additional benefit of stand-off Raman detection. They potentially provide a real-time calibration of the system sensitivity. Real time sensitivity calibration is important for quantitative analysis the contaminants based on the intensity of their Raman lines. In addition, the use of the 266 nm wavelength allows for exploitation of the signal enhancement characteristics associated with solar-blind lidar systems.

Figure 13:
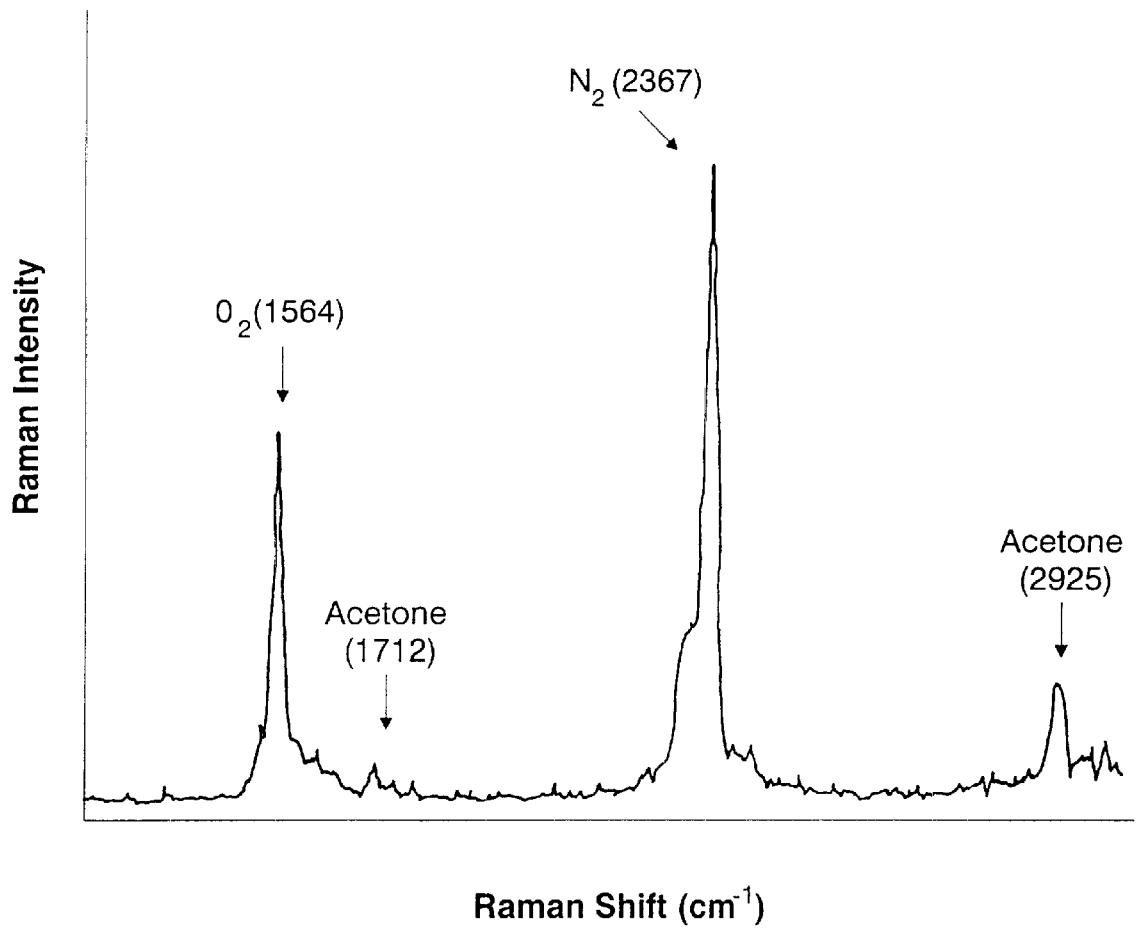
FIG. 13 is a graphical representation of field test results of the sensor of the present invention interrogating acetone contained in an open pan.

The field test of the sensor was also conducted using acetone in an open pan as the test substance. The stand-off distance was 5 meters and the integration time was 8 minutes. The results were displayed graphically as shown in FIG. 13.

Laboratory testing of a Ramon based sensor to detect and identify biological and chemical substances was conducted in the laboratory. The sensor tested included the portable unit constructed generally as set forth above with reference to the preferred embodiment. The optical beam transmitter included 244 nm frequency doubled argon-ion laser with a power of 50 mW. The optical detector included a 6-inch diameter Newtonian telescope. A filter to reject elastically scattered light included a sharp-cut interference filter. A single stage 0.25 m spectrometer with a 2380 groove/mm grating blazed for 250 nm served as a spectral resolver for the Raman light. An 18 mm wide CCD detector with intensifier captured a 3500 $cm^{-1}$ wide portion of the Raman spectrum.

This sensor configuration set forth above was used to interrogate B. thuringiensis and acetonitrile in aqueous solution. The integration time was 5 minutes, and the standoff distance was 3 m. The results of the scan are graphically set forth in the FIG. 15. Line A indicates the Raman shift for a solution of acetonitrile and water (4% acetonitrile by volume.) Distinctive peaks unique to the chemical are produced and are indicated generally by +. Line B graphically depicts the Raman shift of a water solution of the baterium bacillus thuringiensis. The distinctive peaks unique to the bacterium are indicated by *. The Raman shift for a mixture of both solutions is shown as line C. The signature peaks of both substances represented by +and *respectively, can be seen in Line C. Accordingly, the sensor of the present invention has been shown to be effective in detection, and discrimination between, both chemical and biological substances.

Although the illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. A method for remote, stand-off, in situ spectroscopic detection of a target including a biological substance disposed on a surface comprising the steps of:

providing an optical beam transmitter, and an optical beam detector in a portable instrument to permit transportability of the instrument to a predetermined location;

spacing said transmitter a distance from the surface having the target substance including a biological substance;

transmitting an optical detection beam including at least a laser transmission toward the target substance on the surface;

detecting optical behavior resulting from optical illumination of the target substance on the surface; and analyzing said optical behavior by spectrally resolving inelastically scattered light resulting from optical illumination of the target substance to determine characteristics of the target substance.

2. The method as defined in claim 1, wherein analyzing said optical behavior includes analyzing the Raman shift in order to determine the characteristics of the target substance.

3. The method as defined in claim 1, wherein said distance between said transmitter and the target substance on the surface is less than 5 meters.

4. The method as defined in claim 1, wherein said distance between said transmitter and the target substance on the surface is in the range of approximately 2 to 50 meters.

5. The method as defined in claim 1, further comprising the steps of:
providing an optical detector to detect said optical behavior, and positioning said optical detector adjacent said optical beam transmitter.

6. The method as defined in claim 5, further comprising the step of establishing a co-linear optical transmission/detection path between, said optical beam transmitter and said optical detector and the substance.

7. The method as defined in claim 5, wherein the laser transmission has a wavelength of approximately 244 nm.

8. The method as defined in claim 1, further comprising the steps of providing a range finding device and determining the distance from the instrument to the target substance to enhance optical detection of behavior resulting from optical illumination of the target substance on the surface.

9. A method for remote, stand-off, in situ spectroscopic detection of a target biological substance disposed on a surface comprising the steps of:
providing an optical beam transmitter;
spacing said transmitter a distance from the surface having the target biological substance;
transmitting an optical detection beam including at least a laser transmission having a wavelength less than 300 nm toward the target biological substance on the surface;
detecting optical behavior resulting from optical illumination of the target biological substance on the surface; and
analyzing said optical behavior by spectrally resolving inelastically scattered light resulting from optical illumination of the target biological substance to determine characteristics of the target biological substance.

10. A method for remote, stand-off, and high efficiency spectroscopic detection of biological substances, comprising:
establishing a co-linear opticaltransmission/detection path between, a combination optical beam transmitter and spectral analyzer and a target including a biological substance;
transmitting an optical detection beam comprising at least a laser transmission along said path to illuminate said target;
detecting optical behavior resulting from bombardment of the target within said optical detection path; and
analyzing said optical behavior whereby characteristics of the target are detected.

11. The method as defined in claim 10 wherein said co-linear optical transmission/detection path comprises a transmitted optical beam which is co-axial with an optical detection path.

12. The method as defined in claim 10 wherein said establishing comprises fixing a laser beam transmitter sufficiently proximal an optical telescope to direct a laser beam to said target within the optical path of said telescope.

13. The method as defined in claim 12 wherein said laser beam is directed within said optical path by turning said beam at least one time with a beam-directing surface after emission from said laser beam transmitter.

14. The method as defined in claim 13 wherein turning comprises first reflecting said beam substantially perpendicularly from its path of emission into said optical path, followed by a second reflecting of said beam substantially perpendicular from a beam path resulting from its first reflecting whereby said beam is established co-linearly along said optical transmission/detection path.

15. The method as defined in claim 10 wherein detecting comprises gathering said optical behavior through a telescopic lens and directing said detected optical behavior for analysis.

16. The method as defined in claim 15 wherein said detecting further comprises directing said optical behavior to an optical enhancer before analysis.

17. The method as defined in claim 10, wherein said analyzing comprises converting said optical behavior to spectral information whereby said target characteristics are detected.

18. The method as defined in claim 17, including providing a transducer for converting said spectral information to electrical signals for analysis by a computer.

19. The method as defined in claim 10, wherein analyzing includes spectrally resolving inelastically scattered light resulting from bombardment of the target to determine the composition of the target.

20. The method as defined in claim 10, wherein analyzing includes determining the polarization of elastically scattered light reflected from the target in order to determine the presence of contamination.

21. An apparatus for remote, stand-off, and high efficiency spectroscopic detection of biological and/or chemical substances, comprising:
an optical beam transmitter which transmits a beam having an axis of transmission to a target, said beam comprising at least a laser emission;
an optical detector which gathers optical information and has an optical detection path to the target, said path having an axis of optical detection;
a beam alignment device which fixes said transmitter proximal to said detector and directs said beam to the target along said optical detection path such that said axis of transmission is substantially co-linear with said axis of optical detection; and
an analyzer operatively connected to said detector for receipt of optical information and analysis of same.

22. The apparatus as defined in claim 21, wherein said beam alignment device includes a first beam directing element for directionally altering said beam.

23. The apparatus as defined in claim 22, wherein said beam alignment device includes a second beam directing element for further directionally altering said beam, and wherein said first beam directing element directs said beam emitted from said optical beam transmitter at an angle such that said beam crosses into said optical detection path, and said second beam directing element further directs said beam toward the target.

24. The apparatus as defined in claim 21, wherein said analyzer includes a spectrometer for creating a spectrum by resolving by wavelength scattered light energy and a transducer for converting the spectrum into electrical signals.

25. The apparatus as defined in claim 21, wherein said optical detector includes a telescope having a collecting end and a transmitting end, and the apparatus further includes a filter for rejecting unwanted light energy, said filter being disposed adjacent and operatively connected to the transmission end of said telescope.

26. The apparatus as defined in claim 25, wherein said analyzer includes a spectrum generator for producing a spectrum, said spectrum generator being disposed adjacent and operatively connected to said filter such that light energy passing through said filter may be spectrally resolved by said spectrum generator.

27. The apparatus as defined in claim 26, wherein said analyzer further includes a transducer for converting light energy into electric signals, said transducer being disposed adjacent and operatively connected to said spectrum generator such that transducer converts the spectrum into electrical signals for processing by a computer.

28. The apparatus as defined in claim 21 wherein said laser emission has a wavelength of approximately 244 nm.

29. A portable sensor for determining the composition of a target including a biological and/or chemical substance spaced a distance from the sensor through Raman spectroscopy comprising:

an optical beam transmitter which transmits a beam having an axis of transmission to the target, said beam comprising at least a laser emission;

an optical detector which gathers optical information and has an optical detection path to the target, said path having an axis of optical detection;

a beam alignment device which fixes said transmitter proximal to said detector and directs said beam to the target along said optical detection path such that said axis of transmission is substantially co-linear with said axis of optical detection;

an analyzer operatively connected to said detector for receipt of optical information and analysis of same; and a rigid platform wherein said optical beam transmitter, said optical detector, said beam alignment device, and said analyzer are secured to said platform such that said sensor may be easily transported to a site and aimed toward a target.

30. A method for remote, stand-off, in situ spectroscopic detection of a target substance disposed on a surface comprising the steps of:

providing an optical beam transmitter, and an optical beam detector in a portable instrument to permit transportability of the instrument to a predetermined location;

spacing said transmitter a distance from the surface having the target substance including a biological substance;

establishing a co-linear optical transmission/detection path between, said optical beam transmitter and said optical detector and the substance transmitting an optical detection beam including at least a laser transmission toward the target substance on the surface;

detecting optical behavior resulting from optical illumination of the target substance on the surface; and analyzing said optical behavior by spectrally resolving inelastically scattered light resulting from optical illumination of the target substance to determine characteristics of the target substance.

31. A method for remote, stand-off, and high efficiency spectroscopic detection of solids, liquids and gases, comprising the steps of:

establishing a co-linear optical transmission/detection path between, a combination optical beam transmitter and spectral analyzer and a target wherein said co-linear optical transmission/detection path includes a transmitted optical beam having an axis which is substantially co-linear with an axis of optical detection;

transmitting an optical detection beam including at least a laser transmission along said path to illuminate said target;

detecting optical behavior resulting from bombardment of the target within said optical detection path; and analyzing said optical behavior whereby characteristics of the target are detected.

* * * * *